US012746378B2

(12) United States Patent
Daviot et al.

(10) Patent No.: US 12,746,378 B2
(45) Date of Patent: Sep. 29, 2026

(54) MICRONEEDLE APPLICATOR

(71) Applicant: APTAR FRANCE SAS, Le Neubourg (FR)

(72) Inventors: Stéphane Daviot, Graveron Semerville (FR); Francis Moreau, Sotteville les Rouen (FR)

(73) Assignee: APTAR FRANCE SAS, Le Neubourg (FR)

(*) Notice: Subject to any disclaimer, the term of this patent is extended or adjusted under 35 U.S.C. 154(b) by 873 days.

(21) Appl. No.: 18/007,666

(22) PCT Filed: Jun. 1, 2021

(86) PCT No.: PCT/FR2021/050990
§ 371 (c)(1),
(2) Date: Dec. 1, 2022

(87) PCT Pub. No.: WO2021/245348
PCT Pub. Date: Dec. 9, 2021

(65) Prior Publication Data

US 2023/0264005 A1 Aug. 24, 2023

(30) Foreign Application Priority Data

Jun. 2, 2020 (FR) ....................................... 2005785

(51) Int. Cl.
*A61M 37/00* (2006.01)

(52) U.S. Cl.
CPC ............................... *A61M 37/0015* (2013.01)

(58) Field of Classification Search
CPC ............. B05B 11/0038; B05B 11/0054; B05B 11/1028; B05B 11/1033; B05B 11/1035;
(Continued)

(56) References Cited

U.S. PATENT DOCUMENTS

2007/0250018 A1* 10/2007 Adachi ............. A61M 37/0015 604/239
2012/0109065 A1* 5/2012 Backes ............. A61M 37/0015 604/173

(Continued)

FOREIGN PATENT DOCUMENTS

CN 204293680 U 4/2015
KR 10-1492732 B1 2/2015

OTHER PUBLICATIONS

International Search Report for PCT/FR2021/050990 dated Sep. 29, 2021.

(Continued)

*Primary Examiner* — Majid Jamialahmadi
(74) *Attorney, Agent, or Firm* — Sughrue Mion, PLLC

(57) ABSTRACT

A microneedle applicator for applying a fluid product to the skin and causing the fluid product to penetrate to the skin. The applicator has an application face provided with a fluid product outlet and a plurality of microneedles; a motor for causing the microneedles to vibrate; a fluid product reservoir connected to the outlet; and a manual actuating member for conveying the fluid product from the reservoir to the outlet. The applicator has two distinct modules removably connected to each other, namely, a first module housing the motor; and a second module housing the fluid product reservoir and forming the application face and the actuating member, the actuating member being accessible and manually manipulable when the two modules are connected to each other.

17 Claims, 4 Drawing Sheets

(58) Field of Classification Search
CPC .... A61M 2037/0023; A61M 2037/003; A61M 2037/0038; A61M 2037/0061; A61M 37/0015; A61M 5/46; A61B 2218/002; A61B 2018/143
See application file for complete search history.

(56) References Cited

U.S. PATENT DOCUMENTS

| | | | | |
|---|---|---|---|---|
| 2015/0344834 | A1 | 12/2015 | Mitragotri et al. | |
| 2016/0030073 | A1* | 2/2016 | Isakov | A61B 17/221<br>606/113 |
| 2017/0354810 | A1* | 12/2017 | O'Brien, III | A61M 5/46 |

OTHER PUBLICATIONS

International Preliminary Report on Patentability issued May 2, 2022, in International Application No. PCT/FR2021/050990.

* cited by examiner

MICRONEEDLE APPLICATOR

CROSS REFERENCE TO RELATED APPLICATIONS

This application is a National Stage of International Application No. PCT/FR2021/050990 filed Jun. 1, 2021, claiming priority based on French Patent Application No. 2005785 filed Jun. 2, 2020.

The present invention relates to a microneedle applicator for applying a fluid product on the skin and for making it penetrate into the upper layer of the epidermis. The field of application of the invention is that of cosmetics, and not that of tattooing. The aim is to reinforce the effectiveness of a cosmetic treatment in the skin, and not to colour the skin.

Conventionally, this type of cosmetic applicator comprises an application face provided with at least one fluid product outlet and with a plurality of microneedles. A motor, often electric, is used to make the microneedles vibrate, individually or with the application face. A fluid product reservoir is connected to the fluid product outlet. The reservoir can be integrated or not to the applicator. When it is integrated, the question is thus asked about it being filled or it being replaced. The applicator can be dismountable or comprise a window for accessing the reservoir.

On the other hand, an actuating member is also provided to convey the fluid product from the fluid product reservoir to the fluid product outlet. This actuating member is often the component which also controls the motor, which thus accumulates a dual function, namely, to make the microneedles vibrate and to convey the fluid product from the reservoir to the application face.

The present invention aims to propose a very simple applicator, just as good in terms of design and use, with a simple and intuitive fluid product distribution.

To achieve this aim, the applicator of the present invention comprises two distinct modules axially and removably connected to each other, namely:

- a motor module housing the motor and the accessories to make the motor function; and
- a second module housing the fluid product reservoir and forming the application face and the actuating member, the manual actuating member being accessible and manually manipulable when the two modules are connected to each other.

The fluid product distribution is therefore manually managed by the user who acts using a finger on the actuating member. It is thus understood that the second module is technically very simple, since it comprises no electric or electronic component. It is an inexpensive replaceable cartridge, which the user can easily separate and connect to the first module, which integrates the motor, its power supply and control, and is therefore a complex and expensive module. This separation of the applicator into two separate modules, one very simple and inexpensive and the other complex and expensive, is made possible by the manual actuation of the cosmetic product dispenser by the user.

Advantageously, the fluid product reservoir has a variable volume, the movement of the actuating member leading to a decrease in volume of the fluid product reservoir, such that some of its content is delivered to the fluid product outlet. Thus, the actuating member acts directly on the reservoir without intermediate member, like a pump or a motor.

The actuating member may be a lateral pusher, which may be selected from:

- one or a plurality of pushers with transverse movement with respect to the longitudinal axis X;
- a sliding pusher parallel to the longitudinal axis X, and
- a rotary pusher which rotates around the longitudinal axis X.

Advantageously, the second module may comprise a connection end provided with coupling means to the first module for transmitting the vibrations generated by the motor and transmission means for transmitting the vibrations received by the coupling means to the microneedles. In a particular embodiment, the transmission means may be formed by the reservoir. In some cases, the reservoir may be disengaged from the coupling means between a disengaged rest position and an engaged active position, with the actuating member moving the reservoir to the engaged position. The reservoir thus fulfils another function, namely to transmit the force generated by the motor.

According to another embodiment, the transmission means may comprise a transmission rod, the reservoir extending beside the transmission rod. In a variant, the transmission means may comprise a transmission plate, the fluid product reservoir comprising a flexible pouch resting on the transmission plate, the actuating member squeezing the flexible pouch onto the transmission plate. The transmission means may therefore participate in dispensing the cosmetic product.

According to another characteristic, the reservoir, the actuating member and the fluid product outlet can be made in one piece, for example with an elastomeric material.

The applicator may have a general pen-shaped configuration, adapted to be held between the thumb and middle finger with the actuating member operable by means of the index finger, the first module, and advantageously also the second module, having a substantially triangular cross-section.

According to a practical embodiment, the second module may be removably connected to the first module by a connection combining axial and rotary movement.

According to another aspect, the application face can comprise a plate equipped with microneedles and passed through by the fluid product outlet. The fluid product outlet can also be made at the periphery of the application face.

Advantageously, the applicator can further comprise means for adjusting the penetration depth of the microneedles, acting advantageously on the axial position of the motor in the first module. Indeed, it is sometimes useful to make the microneedles penetrate more or less, according to the cosmetic product, to the desired treatment or the quality and the nature of the skin.

The applicator can also comprise means for controlling the motor, which deactivate it automatically when the two modules are not connected. This is for safe use.

The scope of the invention resides in constituting a replaceable and therefore inexpensive module, in the manner of a cartridge which does not incorporate any active (electrical) components: the simplicity of this module results from the use of a manual actuating member, which preferably acts directly on the volume of the reservoir.

The invention will now be fully described in reference to the appended drawings which give, as non-limiting examples, a plurality of embodiments of the invention.

In the figures:

FIG. 1*a* is a vertical cross-sectional view through an applicator of the invention, in the disassembled state;

FIG. 1*b* is a large-scale view of a detail in FIG. 1*a;*

Figure 1A:
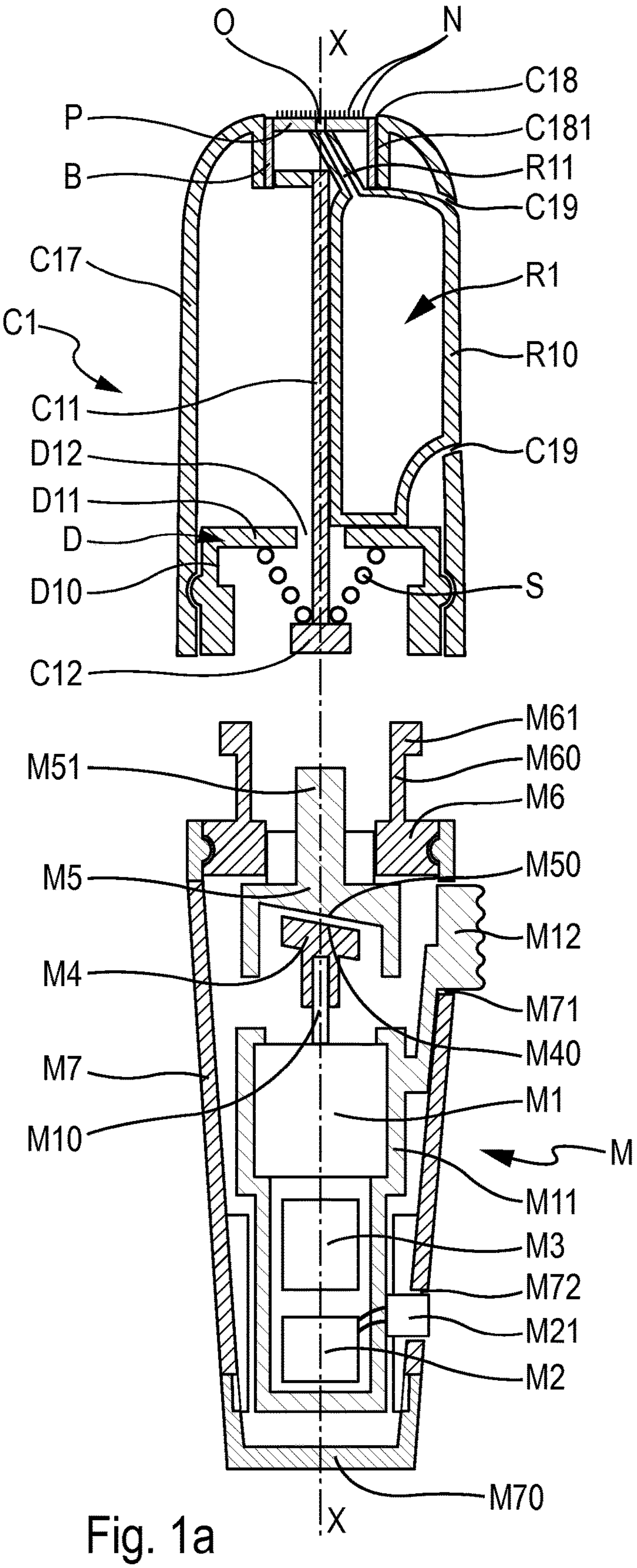
Figure 1B:
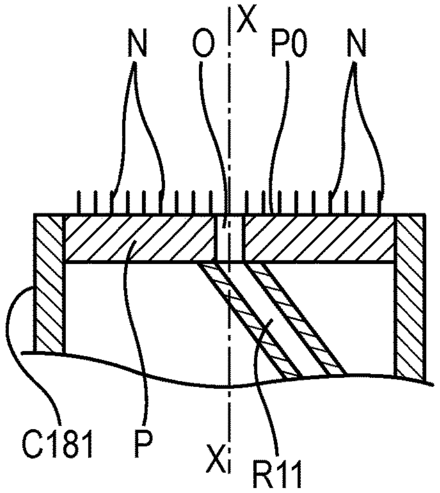
Figure 2:
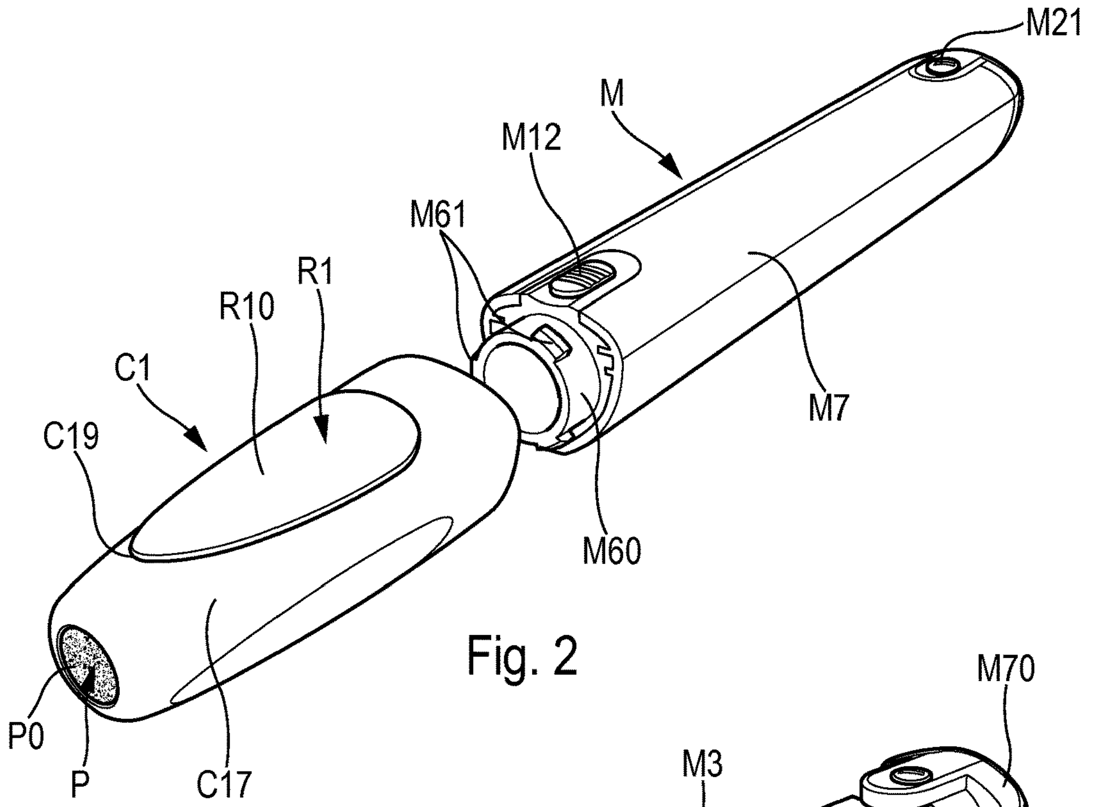
FIG. 2 is a perspective view of the applicator in FIG. 1.
Figure 3:
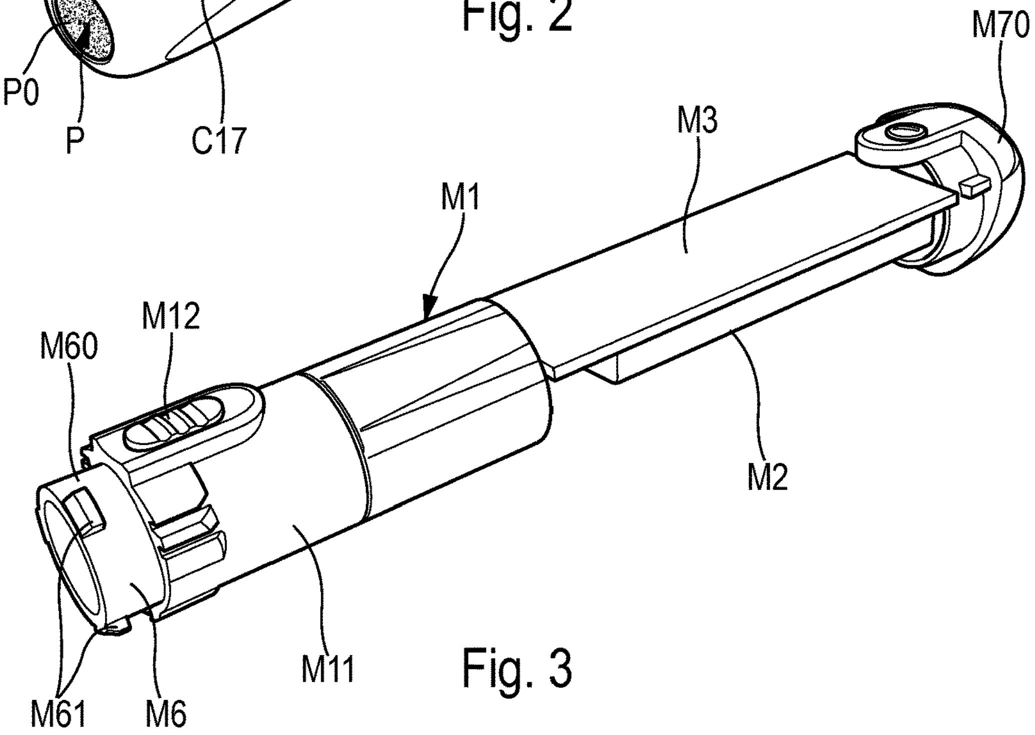
FIG. 3 is a perspective view of a portion of the second module of the applicator in FIGS. 1 and 2.
Figure 4:
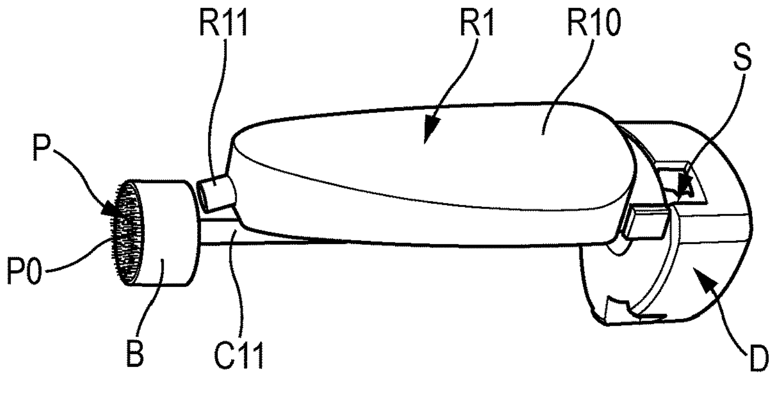
FIG. 4 is a perspective view of a portion of the first module of the applicator in FIGS. 1 and 2.

The applicator of the invention is purely cosmetic, even dermatological, excluding tattooing. It associates two treatment means, namely the distribution of a cosmetic product, which can be a cream, a balm, a lotion, a serum, etc., and the perforation of the epidermis, without touching the dermis, by means of microneedles. According to the nature of the cosmetic product and the result sought, the cosmetic product is applied before, at the same time or after the microperforation. The applicator of the invention is rather for domestic use, in that the user of the applicator will use it on itself. It can, however, be used professionally.

Reference is made firstly to FIGS. 1*a*, 1*b*, 2, 3 and 4 in order to describe in detail the first embodiment of the invention. The applicator of the invention comprises two distinct modules, namely a first module M and a second module C1, which can be connected and disconnected simply and rapidly, by the user themselves, for example using both their hands by impressing a torque and/or a thrust/traction between two modules. When the two modules are assembled, the applicator has a general, pen-shaped configuration with a longitudinal axis X. The applicator can moreover be held in the same way as a pen, held between the thumb and the middle finger with the index finger resting on the applicator.

The first module M comprises an outer shell M7 of substantially cylindrical shape or slightly frustoconical. Its cross-section may be substantially triangular in shape. At its upper end, the shell M7 is open, and closed at its lower end by a fitted bottom wall M70. The shell M7 may comprise two side windows M71 and M72 for receiving two control buttons M71 and M21, as described below.

The first module M contains a motor M1, preferably an electric motor. It can be a small rotary motor which rotates a shaft M10 on itself. An electromagnet motor can also be provided, a linear or a piezoelectric motor. The motor M1 is powered by a battery M2 and controlled by electronics M3, which will manage the rotation speed of the shaft M10, the activation sequences and durations of the motor, etc. An outer activation button M21, which is accessible through the side window M71 which is situated in the proximity of the bottom M70, allows the user to switch the applicator on. The free end of the shaft M10 is covered by an oscillating cap M4, which forms a sloped cam surface M40. The rotation of the shaft M10 drives this sloping cam surface in rotation around its own axis, thus describing a rotary oscillating movement.

Advantageously, the motor M1, the battery M2, the electronics M3 and the oscillating cap M4 are mounted on a mobile carriage M11 along the longitudinal axis X. The mobile carriage M11 comprises a selection slider M12, accessible through the side window M72, which allows the user to set or adjust the penetration depth of the microneedles, as described below. However, the mobile carriage is optional.

The first module M also comprises a piston M4 which moves axially back and forth. The piston M4 forms a sloped lower face M50 which is engaged with the sloped cam surface M40 of the oscillating cap M4. The piston M5 is prevented from rotating, so that the sloped lower face M50 remains stationary, while the sloped cam surface M40 is driven in rotation by the motor M1. As a result, the piston M5 is driven in axial movement, due to the oscillating contact between the cam surface M40 and the sloped face M50. The piston M5 has a transmission head M51, located opposite the sloped face M50 which therefore moves axially back and forth when the motor M1 is activated.

The first module M also comprises a connector endpiece M6 which forms a connection bushing M60 provided with connecting profiles M61. The connector endpiece M6 is securely mounted in the shell M7, e.g., by snap-fastening. The piston M5 passes through the connector endpiece M6, the transmission head M51 of which extends into the connection bushing M60. The piston M5 may be guided axially in the connector endpiece M6 so that it is prevented from rotating. It can thus be said that the piston M5 may slide axially back and forth in the connector endpiece M6. However, the axial stroke of the piston M5 is limited downwards by the oscillating cap M4 and upwards by the connector endpiece M6. The piston M5 is therefore wedged between the cap M4 and the endpiece M6 with a purely axial degree of freedom, imposed by the oscillating cap M4. The piston stroke may be increased or decreased by acting on the selection slider M12 which moves the oscillating cap M4 in relation to the connector endpiece M6 which remains fixed.

It is understood that this first module M contains expensive members and components, which are intended to be kept for a long time.

The second module C1 of the first embodiment comprises an outer casing C17 which is substantially cylindrical or slightly frustoconical. Its cross-section may be substantially triangular in shape, complementary to that of the shell M7 of the first module M. The casing C17 forms a central window C18 at its upper end and is open at its lower end. The central window C18 may form an axial guide cylinder 181. The casing C17 has a side window C19 for receiving the actuating member R10 of the reservoir R, as described below.

The second module C1 comprises a plate P forming an outer application face PO on which microneedles N are arranged. Their number may vary from 5 to 100. Their thickness may vary from 0.05 mm to 0.5 mm. Their length may vary from 0.1 mm to 0.7 mm. These values are given for information purposes only. A fluid product outlet 0 passes through the plate P, which may be central or offset. Alternatively, a plurality of fluid product outlets may be provided, e.g., arranged in a circle. The fluid product outlet may also be at the periphery of the plate P. Optionally, the outlets may be present near and function via the hollow microneedles. In actual fact, the design of the application face PO is not critical to the invention, providing it has microneedles N and allows fluid product to be dispensed.

The plate P is mounted on or in a support ring B to which a transmission rod C11 is attached which extends axially in a central manner. The transmission rod C11 comprises a contact stub C12 intended to come into pressed contact with the transmission head M51 of the first module M.

The second module C1 also comprises a connection sleeve D which is securely mounted in the lower opening of the outer casing C17, e.g., by snap-fastening. This sleeve D comprises a connection housing D10 adapted to receive the connection profiles M61 of the connection bushing M60. The sleeve D also comprises an annular flange D11 which forms a central passage D12, through which the transmission rod C11 passes. The contact stub C12 is arranged in the sleeve D, with a return spring S supported between the stub C11 and the flange D11, such that the plate P is urged towards the inside of the window C18.

The second module C1 also comprises a cosmetic fluid product reservoir R1 which is connected to the fluid product outlet O by a supply duct R11. The reservoir R1 comprises an actuating wall R10 that is accessible through the side window C19 of the casing C17. The actuating wall R10 is deformable, elastically or permanently. Pressure exerted by a user's finger, generally the index finger, has the effect of reducing the useful volume of the reservoir R1 and pressurising its contents, which leads to a portion of its contents being delivered through the supply duct R11 which opens out at the fluid product outlet O. A dose of fluid is thus dispensed onto the application face PO.

The reservoir R1 may be made as a single piece from a suitable plastic material, such as an elastomer. Its actuating wall R10 may have a thinner wall to give it greater elasticity. The reservoir R1 is located beside the transmission rod C11, on the right-hand side in FIG. 1*a*. Alternatively, the reservoir R1 may partially or completely surround the transmission rod C11. Two opposing actuating walls may be provided that the user may press down between thumb and index finger or middle finger.

The second module C1, thanks to its simplicity of design and passivity (no electrical or electronic components), constitutes a low-cost entity, which may be considered as a replaceable cartridge or a replaceable refill. The applicator may, for example, be marketed as a kit comprising a first module M and a plurality of second modules C11. Protection may be sought for such a kit.

In terms of function, it can be said that the second module C1 comprises an actuating member R10, in the form of the flexible wall of the reservoir R1, which makes it possible to dispense the fluid product at the application face PO. This actuating member acts directly on the reservoir R1, without any intermediary. It is accessible when the two modules are connected to each other. The user may operate it manually with one or more fingers.

To connect the second module C1 to the first module M, it suffices to axially engage the connection bushing M60 in the connection sleeve D. In doing so, the transmission head M51 of the piston M5 will come into contact with the contact stub C12 of the transmission rod C11. The spring S will eventually be compressed. When the connection profiles M61 are in abutment with the annular flange D11, the user can make a rotating movement to one of the modules to lock the connection profiles M61 in the connection housing D10 of the sleeve D. A slight tactile and/or audible "click" may indicate that the connection is complete.

The user may then select the penetration depth of the microneedles by acting on the slider M12. It can press the actuating wall R10 to dispense a dose of the cosmetic fluid product at the application face PO. Pressing the activation button M21 activates the motor, which causes the oscillating cap M4 to rotate, which moves the piston M5 back and forth axially, which presses the stub C12 against the spring S. The rod C11 transmits the vibration to the plate P with its microneedles N, which pierce the surface layer of the user's skin, which is already coated with the cosmetic fluid product. The fluid product thus penetrates the skin superficially for an enhanced action.

It is advantageous to provide the electronics M3 with a shut-off of the motor M1 in the event that the second module C1 is not connected to the first module M.

Reference is now made to FIGS. 5 to 10 to describe a plurality of embodiments for the second applicator module, particularly in terms of the fluid product reservoir, its actuating member and the transmission of the vibration between the contact stub and the plate. These embodiments aim to show that the reservoir may be operated in various ways and even perform a transmission function. The vibrations can also be used to dispense the fluid product from the reservoir. The second modules in FIGS. 5 to 10 are adapted to be connected to the first module M of the first embodiment.

Figure 5:
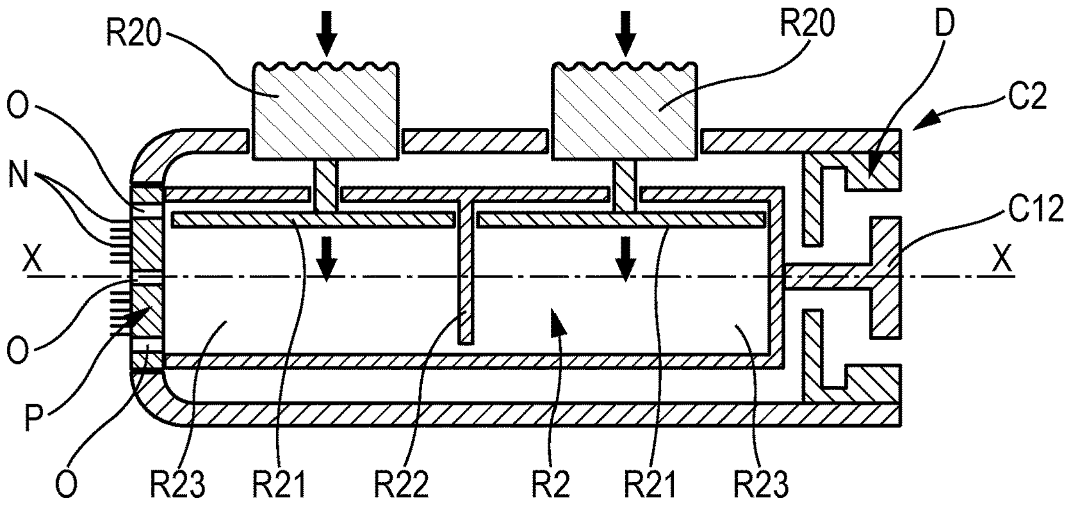
FIGS. 5 to 9 are diagrammatic cross-sectional views through second modules according to six embodiments which are different from the invention.

FIG. 5 shows a second module C2 with a plate P and a sleeve D comparable or identical to that of the first embodiment. However, the reservoir R2 is different, since it is rigid, but comprises two compartments R23 separated by a partition R22, which still allows communication between them. This module C2 comprises two pushers R20 connected respectively to two pistons R21. When a pusher R20 is pressed, a dose of fluid product is delivered through the plate P. The dose corresponds to approximately half of the capacity of the reservoir. Of course, only one pusher R20 can be provided, or possibly more than two. It should also be noted that it is the reservoir R2 which fulfils the function of the transmission rod C11 of the first embodiment by transmitting to the plate P, the vibrations received by the contact stub C12. Alternatively, the compartmentalised reservoir may be formed by a flexible pouch which is squeezed by the pistons R21.

Figure 6A:
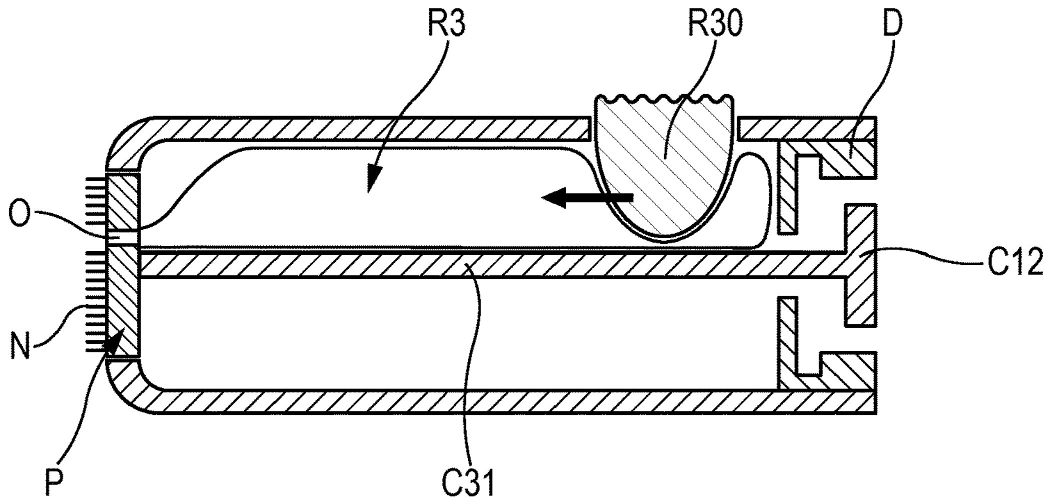
Figure 6B:
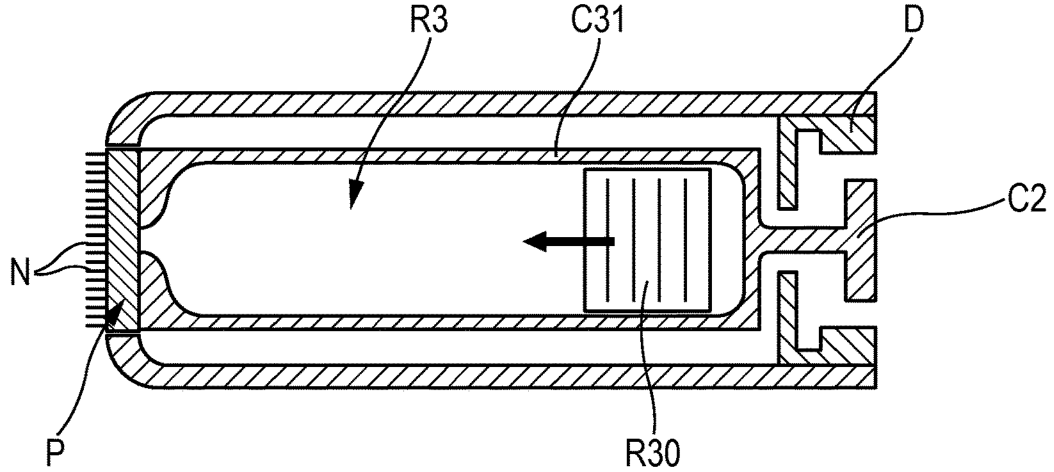

FIGS. 6*a* and 6*b* show another second module C3, in which the reservoir R3 comprises a flexible pouch which may be squeezed by means of a slider R30. The flexible pouch rests on a transmission plate C31, which performs the same function as the transmission rod C11 of the first embodiment. The movement of the slider R30 can be perfectly linear or, on the contrary, jerky with notches to define doses of the fluid product.

Figure 7:
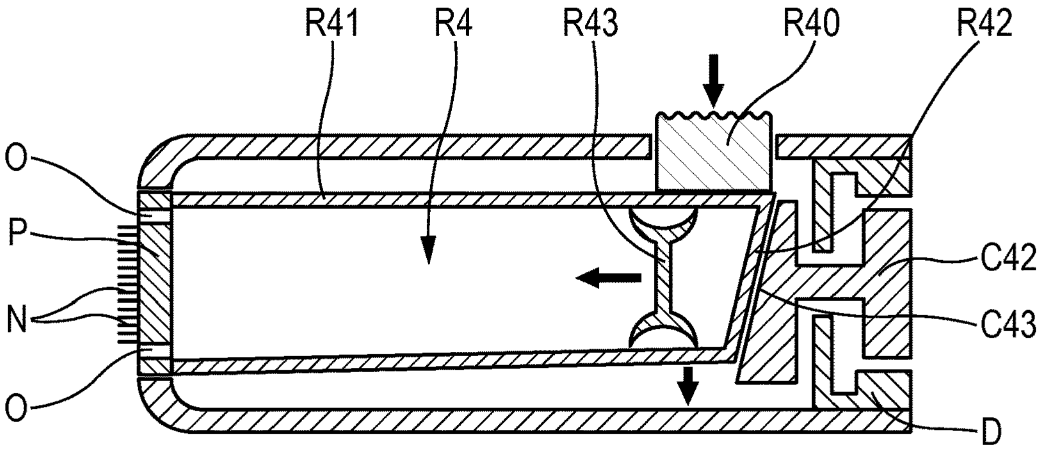

FIG. 7 shows another second module C4, in which the reservoir R4 comprises a sliding cylinder R41, which is mounted so that it can pivot slightly when connected to the plate P. The cylinder R41 comprises a bevelled bottom R42 which can be selectively engaged with a bevelled surface C43 of the contact stub C42. A pusher R40 allows the cylinder R41 to be rotated to move the bottom R41 into contact with the bevelled surface C43 and thus establish continuing transmission. The cylinder contains a pusher piston R43 which moves in the cylinder R41 towards the plate P by means of the vibrations generated by the first module M. The reservoir R4 thus fulfils a function of transmission of engageable/disengageable vibration by pressing the pusher.

Figure 8:
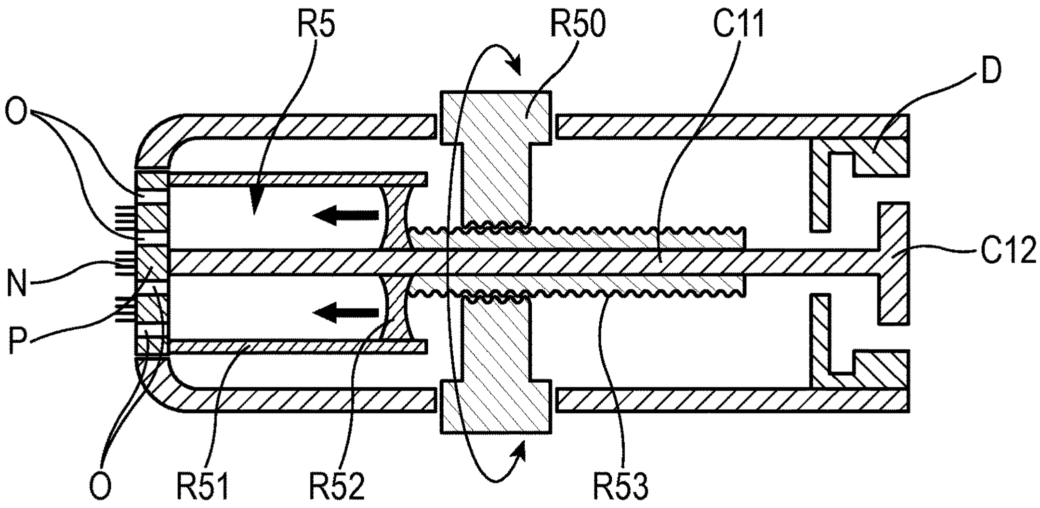

FIG. 8 shows another second module C5, in which the reservoir R5 comprises a sliding cylinder R51, which also performs a vibration transmission function. The cylinder R51 contains a pusher piston R52 which is movable in the cylinder by means of a threaded rod R53 which engages with a rotary actuating ring R50. The movement of the rotary ring R50 may be linear or notched.

Alternatively, the rotary ring may act on the reservoir pusher piston via a rack. It is also possible to imagine that the rotating ring R50 is used to twist a flexible pouch, which may extend beside or around the transmission rod C11.

Figure 9:
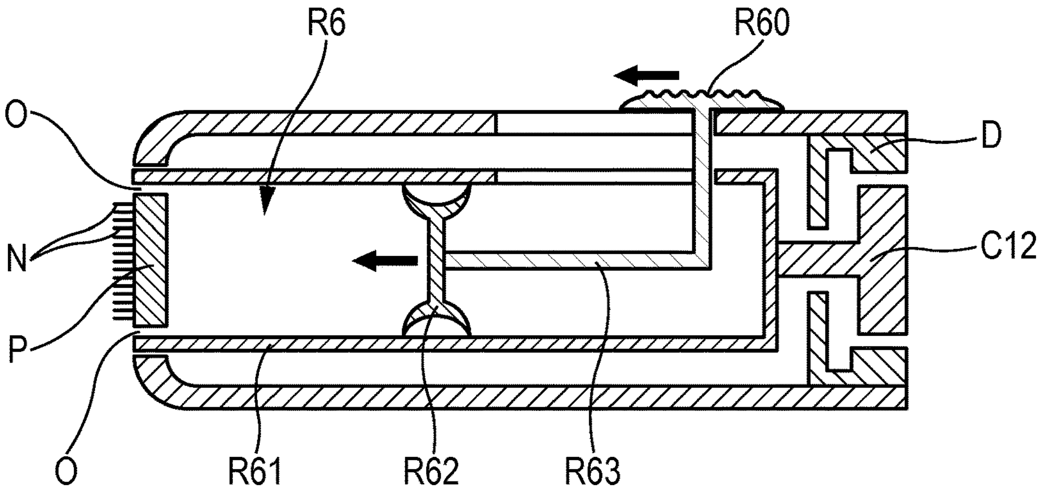

FIG. 9 shows another second module C6, in which the reservoir R6 comprises a sliding cylinder R61, which also performs a vibration transmission function. The cylinder R61 contains a pusher piston R62 which is movable in the cylinder by means of a slider R60 which is connected to the pusher piston R62 by a rail R63.

Via the examples of FIGS. 5 to 10, as well as the first embodiment, it is understood that the reservoir R1, R2, R3, R4, R5, R6 may perform different functions, in addition to its basic function. It can transmit vibrations to the microneedles, be used as a clutch, as a transmission variator or as a penetration variator for the microneedles.

In all embodiments, the second module C1, C2, C3, C4, C5, C6 comprises an actuating member R10, R20, R30, R40, R50, R60 which is accessible and manually manipulable, even when the second module is connected to the first module. It should be observed that the actuating member may be in different forms (pusher, slider, rotating ring) and moves either perpendicularly to the longitudinal axis X, either axially or in rotation. There may be a plurality of actuating members (R20) to define doses. The movement of the actuating member may also be notched. The actuating member may be an integral part of the reservoir or member which is associated with the reservoir.

It should also be noted that the fluid product outlet O may be central, offset, arranged in a single or concentric circle. In FIG. 9, it can be seen that the fluid product outlet O extends all around the plate P which supports the microneedles N. This plate is mounted in the sliding cylinder R61.

The invention thus provides a vibrating microneedle cosmetic product applicator which is designed in the form of two separable modules, namely a "motor" module and a "reservoir/microneedle" module which can be considered as a cartridge or refill, the design of which is simple, making it inexpensive and thus disposable. The pen-shaped design of the applicator also makes it intuitive to use.

The invention claimed is:

1. A microneedle applicator for applying a fluid product on the skin and for causing the fluid product to penetrate into the skin, the applicator defining a longitudinal axis X and comprising:

an application face provided with at least a fluid product outlet and a plurality of microneedles;

a motor for causing the microneedles to vibrate;

a fluid product reservoir connected to the fluid product outlet;

a manual actuating member which acts directly on the volume of the reservoir for conveying the fluid product from the fluid product reservoir to the fluid product outlet, the manual actuating member configured to be actuated by a user's finger pressing on the manual actuating member, wherein the applicator further comprises two distinct modules removably axially connected to one another, namely:

a first module housing the motor and accessories for operating the motor; and a second module housing the fluid product reservoir and forming the application face and the manual actuating member, the manual actuating member being manually accessible and manipulable, when the two modules are connected to each other.

2. The applicator according to claim 1, wherein the fluid product reservoir has a variable volume, the movement of the manual actuating member leading to a decrease in volume of the fluid product reservoir, such that some content is repelled to the fluid product outlet.

3. The applicator according to claim 1, wherein the manual actuating member is a manual lateral pusher.

4. The applicator according to claim 3, wherein the manual lateral pusher is selected from:

one or a plurality of pushers with transverse movement with respect to the longitudinal axis X;

a slider parallel to the longitudinal axis X, and a rotary ring which rotates around the longitudinal axis X.

5. The applicator according to claim 1, wherein the second module comprises a connection end provided with coupling means to the first module for transmitting the vibrations generated by the motor and transmission means for transmitting to the microneedles the vibrations received by the coupling means.

6. The applicator according to claim 5, wherein the transmission means are formed by the fluid product reservoir.

7. The applicator according to claim 6, wherein the fluid product reservoir can be disengaged from the coupling means between a disengaged rest position and an engaged active position, the actuating member moving the fluid product reservoir into the engaged position.

8. The applicator according to claim 5, wherein the transmission means comprises a transmission rod, the fluid product reservoir extending beside the transmission rod.

9. The applicator according to claim 5, wherein the transmission means comprises a transmission plate, the fluid product reservoir comprising a flexible pouch resting on the transmission plate, the actuating member squeezing the flexible pouch onto the transmission plate.

10. The applicator according to claim 1, wherein the reservoir, the actuating member and the fluid product outlet are made as a single part, advantageously with an elastomer.

11. The applicator according to claim 1, having a general pen-shaped configuration, adapted to be held between the thumb and middle finger with the manual actuating member operable by means of the index finger, the first module, and advantageously also the second module, having a substantially triangular cross-section.

12. The applicator according to claim 1, wherein the second module is removably connected to the first module by a connection combining axial and rotary motions.

13. The applicator according to claim 1, wherein the application face comprises a plate equipped with microneedles, and passed through by the fluid product outlet.

14. The applicator according to claim 1, further comprising means for adjusting the penetration depth of the microneedles, acting advantageously on the axial position of the motor in the first module.

15. The applicator according to claim 1, further comprising control means of the motor, which automatically deactivate it when the two modules are not connected.

16. The applicator according to claim 1, wherein the manual actuating member actuates in a direction orthogonal to the longitudinal axis X.

17. The applicator according to claim 1, wherein the manual actuating member actuates in a direction traverse to a longitudinal extension of the plurality of microneedles.

* * * * *